(12) United States Patent
Mihashi et al.

(10) Patent No.: US 7,311,402 B2
(45) Date of Patent: Dec. 25, 2007

(54) EYE OPTICAL CHARACTERISTIC MEASURING INSTRUMENT

(75) Inventors: Toshifumi Mihashi, Tokyo (JP); Yoko Hirohara, Tokyo (JP); Takashi Fujikado, Osaka (JP); Naoyuki Maeda, Osaka (JP)

(73) Assignee: Kabushiki Kaisha Topcon, Tokyo (JP)

( * ) Notice: Subject to any disclaimer, the term of this patent is extended or adjusted under 35 U.S.C. 154(b) by 515 days.

(21) Appl. No.: 10/488,790

(22) PCT Filed: Aug. 9, 2002

(86) PCT No.: PCT/JP02/08197

§ 371 (c)(1),
(2), (4) Date: May 4, 2004

(87) PCT Pub. No.: WO03/022138

PCT Pub. Date: Mar. 20, 2003

(65) Prior Publication Data

US 2005/0073647 A1  Apr. 7, 2005

(30) Foreign Application Priority Data

Sep. 7, 2001 (JP) .............................. 2001-271679

(51) Int. Cl.
*A61B 3/10* (2006.01)
(52) U.S. Cl. ........................ 351/221; 351/205; 351/211
(58) Field of Classification Search ........ 351/200–208, 351/211, 212, 221–223, 243
See application file for complete search history.

(56) References Cited

U.S. PATENT DOCUMENTS 6,234,978 B1  5/2001  Mihashi et al. ............. 600/558

(Continued)

FOREIGN PATENT DOCUMENTS

JP  8-206073 A  8/1996

(Continued)

OTHER PUBLICATIONS

R.A. Applegate et al., "Localized Measurement of Scatter Due to Cataract", IOVS, Mar. 15, 2000, vol. 41, No. 4, 13-B13, p. S3.

(Continued)

*Primary Examiner*—M. Hasan
(74) *Attorney, Agent, or Firm*—Foley & Lardner LLP

(57) ABSTRACT

Scattering can be measured by using an optical system having a Hartman-Shack wave-surface sensor. An eye optical characteristic measuring instrument comprises a light source unit 10 for emitting a light beam of a wavelength in the near-infrared region, an illumination optical system 40 for illuminating a small area of the retinal of an eye to be measured with the light beam from the light source unit 10, a light-receiving optical system 20 for receiving a part of the reflected beam of the light beam from the light source unit 10 reflected from the retina through a converting member for converting the part of the reflected light beam into at least substantially 17 light beams, a light-receiving section 23 for receiving the received light beam directed by the light-receiving optical system 20 and generating a signal, and a calculating unit for determining the wavefront aberration of the light beam entering the light-receiving optical system 20 and the degree of scattering of the received light beam on the basis of the signal from the light-receiving section 23.

14 Claims, 9 Drawing Sheets

U.S. PATENT DOCUMENTS 6,273,566 B1 * 8/2001 Kobayashi et al. ......... 351/221
6,525,883 B2 * 2/2003 Hirohara et al. ............ 359/618

FOREIGN PATENT DOCUMENTS

| JP | 10-305013 A | 11/1998 |
|---|---|---|
| JP | 2001-95760 A | 4/2001 |
| JP | 2001-204690 A | 7/2001 |

OTHER PUBLICATIONS

Kabushiki Kaisha Topcon, Meinicon Co., Ltd., Osaka University, Selective translation of Program and Proceeding of the 37th Japanese Society of Ophthalmologist Optics and 16th Japanese Association of Ophthalmic ME Joint Conference, II-1 "Analysis of Retina Image at Time of Wearing Bi-Focal Contact Lenses," p. 27.

Hoya Healthcare Corporation, Chiba University, Engineering Department, Itabashi Medical Association Hospital Ophthalmology Department, Selective translation of Program and Proceeding of the 37th Japanese Society of Ophthalmologist Optics and 16th Japanese Association of Ophthalmic ME Joint Conference, II-2 "Quantitative Analysis of Far and Near Bi-Focal Increment Refraction Contact Lenses with Space Frequency Characteristic," p. 27.

Asahi Optical Co., Ltd., Optical Research Group, Selective translation of Program and Proceeding of the 37th Japanese Society of Ophthalmologist Optics and 16th Japanese Association of Ophthalmic ME Joint Conference, II-3 "Analysis of Optical Function of Astigmatism Corrective Eye Glasses by Circumflex Lens Meter," p. 28.

Kabushiki Kaisha Topcon, Research Department, Chiba University, Graduate School of Science and Technology, Keio University, Medical School, National Tokyo Medical Center, Selective translation of Program and Proceeding of the 37th Japanese Society of Ophthalmologist Optics and 16th Japanese Association of Ophthalmic ME Joint Conference, II-4 "Human Retina Image Simulation at Defocus and Estimation of Eyesight," p. 28.

Nidek Co., Ltd., Technology Department, Selective translation of Program and Proceeding of the 37th Japanese Society of Ophthalmologist Optics and 16th Japanese Association of Ophthalmic ME Joint Conference, VII-1 "Need for a Change to LOS Standard Data in Cornia-shaped Zernike Polynomial Deployment," p. 41.

Kabushiki Kaisha Topcon, Osaka University, Selective translation of Program and Proceeding of the 37th Japanese Society of Ophthalmologist Optics and 16th Japanese Association of Ophthalmic ME Joint Conference, VII-2 "Application of Spline Function for Ophthalmologic Wave Front Analysis," p. 41.

Kabushiki Kaisha Topcon, Osaka University, Selective translation of Program and Proceeding of the 37th Japanese Society of Ophthalmologist Optics and 16th Japanese Association of Ophthalmic ME Joint Conference, VII-3 "Dispersion Measurement by Hartmann-Shack Wave Front Sensor," p. 42.

Osaka University, School of Ophthalmology, Kabushiki Kaisha Topcon, Selective translation of Program and Proceeding of the 37th Japanese Society of Ophthalmologist Optics and 16th Japanese Association of Ophthalmic ME Joint Conference, VII-4 "Quantification of Dispersion of Cataract by Wave Front Sensor," p. 42.

Osaka University, Selective translation of Program and Proceeding of the 37th Japanese Society of Ophthalmologist Optics and 16th Japanese Association of Ophthalmic ME Joint Conference, Laser Refraction Corrective Surgery Lecture "LASIK and Wave Front Analysis—This really explains-," p. 51.

Osaka University, Medical School, Selective translation of Program and Proceeding of the 37th Japanese Society of Ophthalmologist Optics and 16th Japanese Association of Ophthalmic ME Joint Conference, "Evaluation of Total Astigmatism and Corneal Astigmatism," p. 53.

* cited by examiner

EYE OPTICAL CHARACTERISTIC MEASURING INSTRUMENT

BACKGROUND OF THE INVENTION

1. Field of the Invention

The present invention relates to an eye optical characteristic measuring apparatus for measuring eye optical characteristics.

2. Description of the Related Art

Since a Hartman-Shack wavefront sensor can accurately measure wavefront aberrations of an eye, it has recently attracted considerable attention. This wavefront sensor can become a necessary apparatus in eye surgery in near future especially for the purpose of the planning and follow-up of cornea refractive surgery.

The measurement of the eye wavefront aberrations by the wavefront sensor is greatly different from the measurement of corneal wavefront aberrations by corneal shape measurement in that the measurement result includes an influence of an intraocular optical system, such as a crystalline lens, on the wavefront aberrations. According to this function, it becomes possible to perform an examination in a case where the crystalline lens has refractive index abnormality due to nuclear cataract or the like or in a case where the shape of a refractive plane of the crystalline lens is largely distorted by lenticonus.

As an object of the eye optical system wave front aberrations measurement, an objective evaluation of visual functions can be named. As the evaluation of the visual functions, a subjective examination has been conventionally recognized as a reliable measurement method as compared with an objective examination. Especially, this is true to such an extent that with respect to an auto-refractometer as a former wavefront sensor, a lens interchange method as the subjective examination is called a gold standard.

When the eye wavefront aberrations measured by the wavefront sensor is compared with corrected eyesight or contrast sensitivity, there is a case where they are fully coincident to each other, and there is a case where they are not coincident to each other especially in, for example, old people. In the case of the inconsistency, there is a case where scattering has a large effect on the eyesight.

SUMMARY OF THE INVENTION

As optical factors to influence the visual functions, scattering of an eye optical system, together with the wavefront aberrations, is conceivable.

In the measurement of eye optical characteristics, in the case of aging, cataract, or the like, light scattering from an eye optical system is large, and for the purpose of the objective evaluation of the visual functions, measurement of the light scattering is necessary in addition to the aberrations. An apparatus is desired which enables simultaneous measurement of the light scattering by an optical system of a Hartman-Shack wavefront sensor which has an established reputation in measurement of the wavefront aberrations. On the other hand, the wavefront aberrations measurement by the Hartman-Shack wavefront sensor is already in practical use.

In view of the above, the present invention has an object to provide an eye optical characteristic measuring apparatus which can accurately evaluate visual functions by enabling a Hartman-Shack wavefront sensor, which has a main object of performing wavefront aberrations measurement, to perform light scattering measurement and by performing the light scattering measurement.

Besides, the invention has an object to provide an eye optical characteristic measuring apparatus which enables simultaneous measurement of scattering of the eye by an optical system of the Hartman-Shack wavefront sensor by developing, as a scattering measurement method by the Hartman-Shack wavefront sensor, a scattering analytic method for estimating a scattering amount from SIR (Scatter Intensity Ratio) of background light of a Hartman image.

Besides, the invention has an object to provide an eye optical characteristic measuring apparatus which can measure wavefront aberrations of a light flux incident on a light receiving optical system and a scattering degree of a received light flux from a distribution of relations between the wavefront aberrations of the light flux incident on the light receiving optical system and a point spread function (PSF) of the received light.

Besides, the invention has an object to provide an eye optical characteristic measuring apparatus which can judge that from a distribution of relations between wavefront aberrations of a light flux incident on a light receiving optical system, a scattering degree of a received light flux and a spot diameter of the received light flux, as the wavefront aberrations of the light flux incident on the light receiving optical system and the scattering degree of the received light flux become high, or as the spot diameter of the received light flux becomes large, an influence of cataract or the like becomes large.

In order to achieve the above objects, according to first solving means of the invention, an eye optical characteristic measuring apparatus includes a light source part for emitting a light flux having a specified wavelength, an illumination optical system for illuminating a minute area on a retina of a subject eye with the light flux from the light source part, a light receiving optical system for receiving a part of a reflected light flux of the light flux emitted from the light source part and reflected by the retina of the subject eye through a conversion member for converting it into at least substantially 17 beams, a light receiving part for receiving a received light flux guided by the light receiving optical system to form a signal, and an arithmetic part for obtaining wavefront aberrations of the light flux incident on the light receiving optical system and a scattering degree of the received light flux on the basis of the signal from the light receiving part.

Besides, according to second solving means of the invention, an eye optical characteristic measuring apparatus includes a light source part for emitting a light flux having a specified wavelength, an illumination optical system for illuminating a minute area on a retina of a subject eye with the light flux from the light source part, a light receiving optical system for receiving a part of a reflected light flux of the light flux emitted from the light source part and reflected by the retina of the subject eye through a conversion member for converting it into at least substantially 17 beams, a light receiving part for receiving a received light flux guided by the light receiving optical system to form a signal, and an arithmetic part for obtaining wavefront aberrations of the light flux incident on the light receiving optical system and a spot diameter of the received light flux on the basis of the signal from the light receiving part.

Besides, according to the invention, in the eye optical characteristic measuring apparatus of the first solving means, the arithmetic part can obtain a distribution of relations between the wavefront aberrations of the light flux incident on the light receiving optical system and the scattering degree of the received light flux. Further, according to the invention, in the eye optical characteristic measuring apparatus as stated above, the arithmetic part can be constructed to judge that as the obtained wavefront aberrations of the light flux incident on the light receiving optical system and the scattering degree of the received light flux become high, the influence of cataract or the like becomes large.

Besides, according to the invention, in the eye optical characteristic measuring apparatus of the second solving means, the arithmetic part can obtain a distribution of relations between the wavefront aberrations of the light flux incident on the light receiving optical system and the spot diameter of the received light flux. Further, according to the invention, in the eye optical characteristic measuring apparatus as stated above, the arithmetic part can be constructed to judge that as the obtained wavefront aberrations of the light flux incident on the light receiving optical system and the spot diameter of the received light flux become large, the influence of cataract or the like becomes large.

Besides, according to the invention, in the eye optical characteristic measuring apparatus of the first solving means, the arithmetic part can obtain a distribution of relations among the wavefront aberrations of the light flux incident on the light receiving optical system, the scattering degree of the received light flux, and a spot diameter of the received light flux. Further, according to the invention, in the eye optical characteristic measuring apparatus as stated above, the arithmetic part can be constructed to judge that as the obtained wavefront aberrations of the light flux incident on the light receiving optical system and the scattering degree of the received light flux become high, or the spot diameter of the received light flux becomes large, the influence of the cataract or the like becomes large.

Further, according to the invention, a display part for displaying the distribution obtained by the arithmetic part, the judgment result and the like, or an output part for outputting them to the outside may be included.

Further, according to third solving means of the invention, an eye optical characteristic measuring apparatus includes a light source part for emitting a light flux having a specified wavelength, an illumination optical system for illuminating a minute area on a retina of a subject eye with the light flux from the light source part, a light receiving optical system for receiving a part of a reflected light flux of the light flux emitted from the light source part and reflected by the retina of the subject eye through a conversion member for converting it into at least substantially 17 beams, a light receiving part for receiving a received light flux guided by the light receiving optical system to form a signal, and an arithmetic part for obtaining a point spread function obtained from wavefront aberrations of the light flux incident on the light receiving optical system and an actually measured spot diameter of the received light flux on the basis of the signal from the light receiving part.

DESCRIPTION OF THE PREFERRED EMBODIMENTS

Hereinafter, embodiments of the present invention will be described in detail with reference to the drawings.

1. Explanation of Principle of Eye Optical Characteristic Measurement

Figure 1:
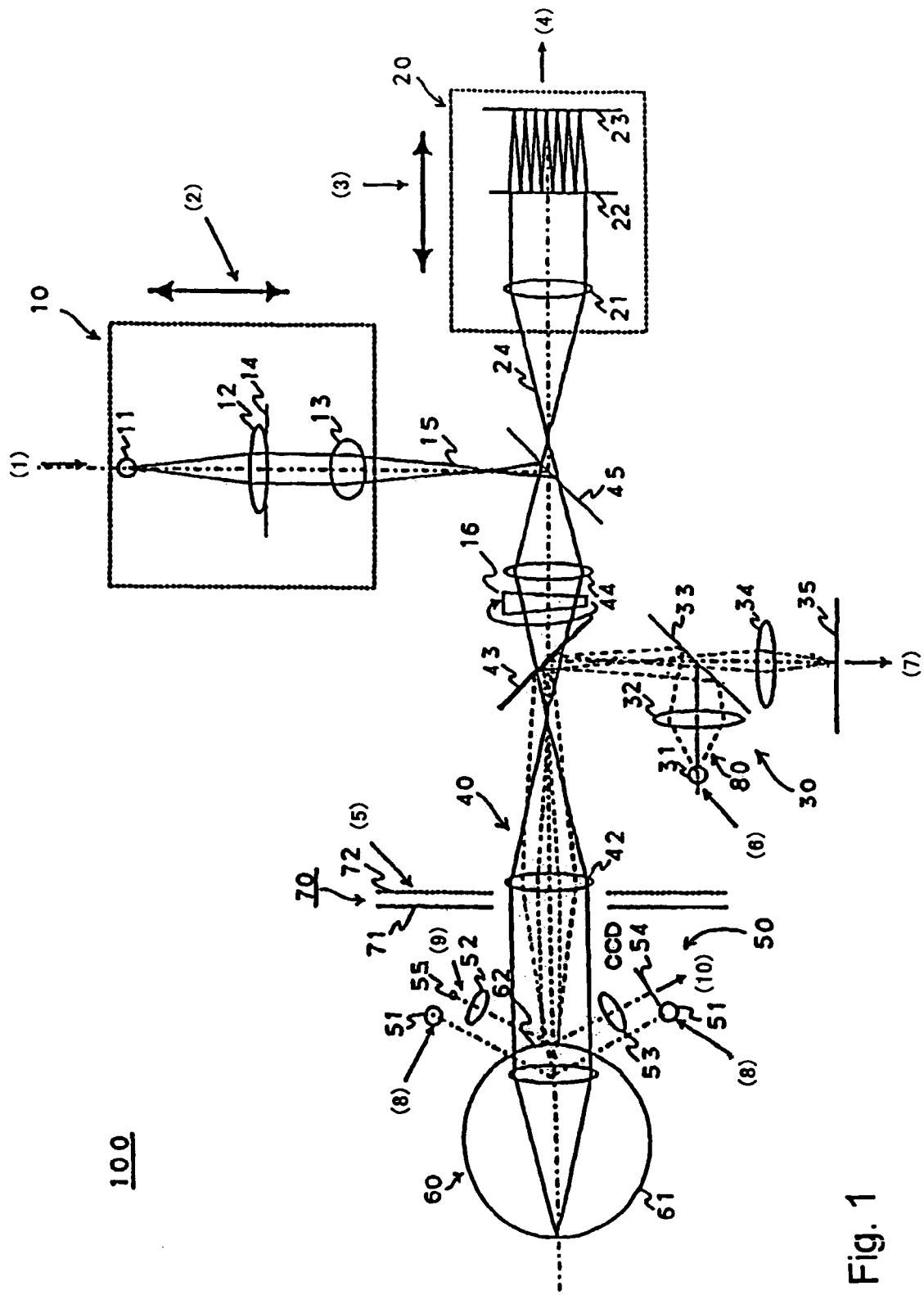
FIG. 1 is a view showing a schematic optical system 100 of an eye optical characteristic measuring apparatus of the invention.

FIG. 1 is a view roughly showing an optical system 100 of an eye optical characteristic measuring apparatus of the invention.

The optical system 100 of the eye optical characteristic measuring apparatus is an apparatus for measuring, for example, an optical characteristic of an eye 60 to be measured as an object, and includes a first illuminating optical system 10, a first light receiving optical system 20, a second light receiving optical system 30, a common optical system 40, an adjusting optical system 50, a second illuminating optical system 70, and a second light sending optical system 80. Incidentally, with respect to the eye 60 to be measured, a retina 61 and a cornea 62 are shown in the drawing.

The first illuminating optical system 10 includes, for example, a first light source part 11 for emitting a light flux of a first wavelength, and a condensing lens 12, and is for illuminating a minute region on the retina (eyeground) 61 of the eye 60 to be measured with the light flux from the first light source part 11 so that its illumination condition can be suitably set. Incidentally, here, as an example, the first wavelength of the illuminating light flux emitted from the first light source part 11 is a wavelength of an infrared range (for example, 780 nm). It is not limited to the wavelength, a illuminating light flux of a specified wavelength can be used.

Besides, it is desirable that the first light source part 11 has a large spatial coherence and a small temporal coherence. Here, the first light source part 11 is, for example, a super luminescence diode (SLD), and a point light source having high luminescence can be obtained.

Incidentally, the first light source part 11 is not limited to the SLD, and for example, a laser having a large spatial coherence and a large temporal coherence can also be used by combining a rotary prism described later. Further, an LED having a small spatial coherence and a small temporal coherence can also be used, if light quantity is sufficient, by inserting, for example, a pinhole or the like at a position of a light source in an optical path.

Besides, in order to uniform the irregular characteristics of reflected light from the retina, a wedge-shaped rotary prism (D prism) 16 is inserted in the illumination optical system. Since an illuminated portion on the retina is operated by the rotation of the rotary prism, the reflected light from the retina becomes uniform, and it is possible to uniform the received light flux (point image) of the light receiving part.

The first light receiving optical system 20 includes, for example, a collimator lens 21, a Hartman plate 22 as a conversion member for converting a part of a light flux (first light flux) reflected and returned from the retina 61 of the eye 60 to be measured into at least 17 beams, and a first light receiving part 23 for receiving the plural beams converted by the Hartman plate 22, and is for guiding the first light flux to the first light receiving part 23. Besides, here, a CCD with little readout noise is adopted for the first light receiving part 23, and as the CCD, a suitable type of CCD, for example, a general low noise type of CCD, a cooling CCD of 1000*1000 elements for measurement, or the like can be applied.

Figure 2:
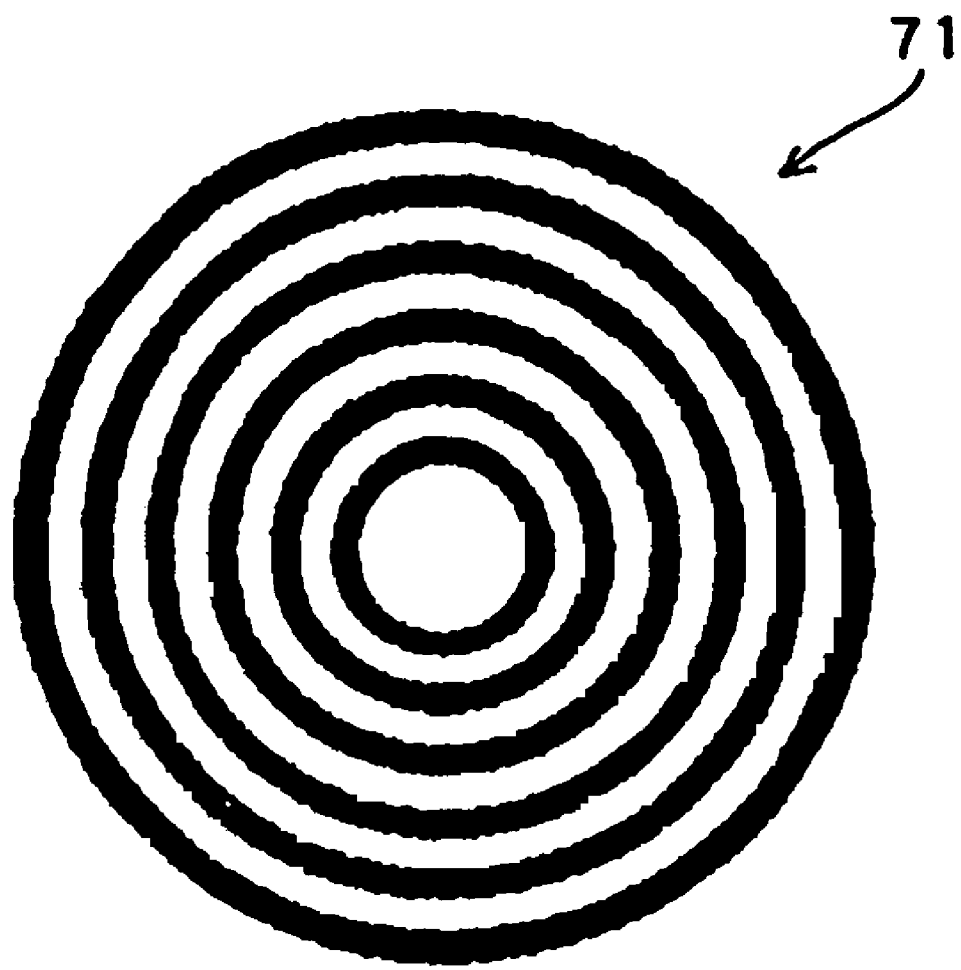
FIG. 2 is a structural view of a Placido disk.

The second illuminating optical system 70 includes a second light source 72 and a Placido's disk 71. Incidentally, the second light source 72 can be omitted. FIG. 2 shows an example of a structural view of the Placido's disk. The Placido's disk 71 is for projecting an index of a pattern composed of plural co-axial rings. Incidentally, the index of the pattern composed of the plural co-axial rings is an example of an index of a specified pattern, and a different suitable pattern can be used. Then, after an alignment adjustment described later is completed, the index of the pattern composed of the plural co-axial rings can be projected.

The second light sending optical system 80 is for mainly performing, for example, the alignment adjustment described later, and measurement and adjustment of a coordinate origin and a coordinate axis, and includes a second light source part 31 for emitting a light flux of a second wavelength, a condensing lens 32, and a beam splitter 33.

The second light receiving optical system 30 includes a condensing lens 34 and a second light receiving part 35. The second light receiving optical system 30 guides a light flux (second light flux), which is originated from the pattern of the Placido's disk 71 illuminated from the second illuminating optical system 70 and is reflected and returned from the anterior eye part or the cornea 62 of the eye 60 to be measured, to the second light receiving part 35. Besides, it can also guide a light flux, which is emitted from the second light source part 31 and is reflected and returned from the cornea 62 of the eye 60 to be measured, to the second light receiving part 35. Incidentally, as the second wavelength of the light flux emitted from the second light source part 31, for example, a wavelength different from the first wavelength (here, 780 nm) and longer than that (for example, 940 nm) can be selected.

The common optical system 40 is disposed on an optical axis of the light flux emitted from the first illuminating optical system 10, can be included in the first and the second illuminating optical systems 10 and 70, the first and the second light receiving optical systems 20 and 30, the second light sending optical system 80 and the like in common, and includes, for example, an a focal lens 42, beam splitters 43 and 45, and a condensing lens 44. The beam splitter 43 is formed of such a mirror (for example, a polarization beam splitter) that the wavelength of the second light source part 31 is sent (reflected) to the eye 60 to be measured, the second light flux reflected and returned from the retina 61 of the eye 60 to be measured is reflected, and the wavelength of the first light source part 11 is transmitted. The beam splitter 45 is formed of such a mirror (for example, a dichroic mirror) that the wavelength of the first light source part 11 is sent (reflected) to the eye 60 to be measured, and the first light flux reflected and returned from the retina 61 of the eye 60 to be measured is transmitted. By the beam splitters 43 and 45, the first and the second light fluxes do not mutually enter the other optical systems to generate noise.

The adjusting optical system 50 is for mainly performing, for example, a working distance adjustment described later, includes a third light source part 51, a fourth light source part 55, condensing lenses 52 and 53, and a third light receiving part 54, and is for mainly performing the working distance adjustment.

Next, the alignment adjustment will be described. The alignment adjustment is mainly carried out by the second light receiving optical system 30 and the second light sending optical system 80.

First, the light flux from the second light source part 31 illuminates the eye 60 to be measured as the object with the substantially parallel light flux through the condensing lens 32, the beam splitters 33 and 43, and the afocal lens 42. The reflected light flux reflected by the cornea 62 of the eye 60 to be measured is emitted as a divergent light flux such as is emitted from a point at the half of the radius of curvature of the cornea 62. The divergence light flux is received as a spot image by the second light receiving part 35 through the afocal lens 42, the beam splitters 43 and 33, and the condensing lens 34.

Here, in the case where the spot image on the second light receiving part 35 deviates from the optical axis, the main body of the eye optical characteristic measuring apparatus is moved and adjusted vertically and horizontally, and the spot image is made to coincide with the optical axis. As stated above, when the spot image coincides with the optical axis, the alignment adjustment is completed. Incidentally, with respect to the alignment adjustment, the cornea 62 of the eye 60 to be measured is illuminated by the third light source 51, and an image of the eye 60 to be measured obtained by this illumination is formed on the second light receiving part 35, and accordingly, this image may be used to make the pupil center coincide with the optical axis.

Next, the working distance adjustment will be described. The working distance adjustment is mainly carried out by the adjusting optical system 50.

First, the working distance adjustment is carried out by, for example, irradiating the eye 60 to be measured with a parallel light flux emitted from the fourth light source part 55 and close to the optical axis, and by receiving the light reflected from the eye 60 to be measured through the condensing lenses 52 and 53 by the third light receiving part 54. Besides, in the case where the eye 60 to be measured is in a suitable working distance, a spot image from the fourth light source part 55 is formed on the optical axis of the third light receiving part 54. On the other hand, in the case where the eye 60 to be measured is out of the suitable working distance, the spot image from the fourth light source part 55 is formed above or below the optical axis of the third light receiving part 54. Incidentally, since the third light receiving part 54 has only to be capable of detecting a change of a light flux position on the plane containing the fourth light source part 55, the optical axis and the third light receiving part 54, for example, a one-dimensional CCD arranged on this plane, a position sensing device (PSD) or the like can be applied.

Next, a positional relation between the first illuminating optical system 10 and the first light receiving optical system 20 will be roughly described.

The beam splitter 45 is inserted in the first light receiving optical system 20, and by this beam splitter 45, the light from the first illuminating optical system 10 is sent to the eye 60 to be measured, and the reflected light from the eye 60 to be measured is transmitted. The first light receiving part 23 included in the first light receiving optical system 20 receives the light transmitted through the Hartman plate 22 as the conversion member and generates a received light signal.

Besides, the first light source part 11 and the retina 61 of the subject eye 60 form a conjugated relation. The retina 61 of the subject eye 60 and the first light receiving part 23 are conjugated. Besides, the Hartman plate 22 and the pupil of the subject eye 60 form a conjugated relation. Further, with respect to the first light receiving optical system 20, the cornea 62 as the anterior eye part of the subject eye 60 and the pupil, and the Hartman plate 22 form a substantially conjugated relation. That is, the front focal point of the afocal lens 42 is substantially coincident with the cornea 62 as the anterior eye part of the subject eye 60 and the pupil. Besides, the plane of the rotary prism 16 inclined with respect to the optical axis is disposed at a substantially conjugated position with respect to the pupil.

Besides, the first illuminating optical system 10 and the first light receiving optical system 20 are moved together so that a signal peak by the reflected light at the first light receiving part 23 becomes maximum on the condition that the light flux from the first light source part 11 is reflected at a point on which it is condensed. Specifically, the first illuminating optical system 10 and the first light receiving optical system 20 are moved in a direction in which the signal peak at the first light receiving part 23 becomes large, and are stopped at a position where the signal peak becomes maximum. By this, the light flux from the first light source part 11 is condensed on the eye 60 to be measured.

The lens 12 converts a diffused light of the light source 11 into a parallel light. A diaphragm 14 is positioned at an optically conjugated position with respect to the pupil of the eye or the Hartman plate 22. The diaphragm 14 has a diameter smaller than an effective range of the Hartman plate 22, and the so-called single path aberrations measurement (method in which the aberrations of the eye has an influence on only the light receiving side) is established. In order to satisfy the above, the lens 13 is disposed such that the conjugated point of the retina of the real light beam coincides with the front focal position, and further, in order to satisfy the conjugated relation between the lens and the pupil of the eye, it is disposed such that the rear focal position coincides with the diaphragm 14.

Besides, after a light beam 15 comes to have a light path common to a light beam 24 by the beam splitter 45, it travels in the same way as the light beam 24 paraxially. However, in the single path measurement, the diameters of the light beams are different from each other, and the beam diameter of the light beam 15 is set to be rather small as compared with the light beam 24. Specifically, the beam diameter of the light beam 15 is, for example, about 1 mm at the pupil position of the eye, and the beam diameter of the light beam 24 can be about 7 mm (incidentally, in the drawing, the light beam 15 from the beam splitter 45 to the retina 61 is omitted).

Next, the Hartman plate 22 as the conversion member will be described.

The Hartman plate 22 included in the first light receiving optical system 20 is a wavefront conversion member for converting a reflected light flux into plural beams. Here, plural micro-Fresnsel disposed on a plane orthogonal to the optical axis are applied to the Hartman plate 22. Besides, in general, with respect to the measuring object part (the eye 60 to be measured), in order to measure a spherical component of the eye 60 to be measured, a third-order astigmatism, and other higher order aberrations, it is necessary to perform the measurement with at least 17 beams through the eye 60 to be measured.

The micro-Fresnel lens is an optical element, and includes, for example, a ring with a height pitch for each wavelength, and a blade optimized for emission parallel to a condensing point. The micro-Fresnel lens here is subjected to, for example, 8-level optical path length variation employing a semiconductor fine working technique, and achieves a high condensing efficiency (for example, 98%).

Besides, the reflected light from the retina 61 of the eye 60 to be measured passes through the afocal lens 42 and the collimate lens 21, and is condensed on the first light receiving part 23 through the Hartman plate 22. Accordingly, the Hartman plate 22 includes a wavefront conversion member for converting the reflected light flux into at least 17 beams.

Figure 3:
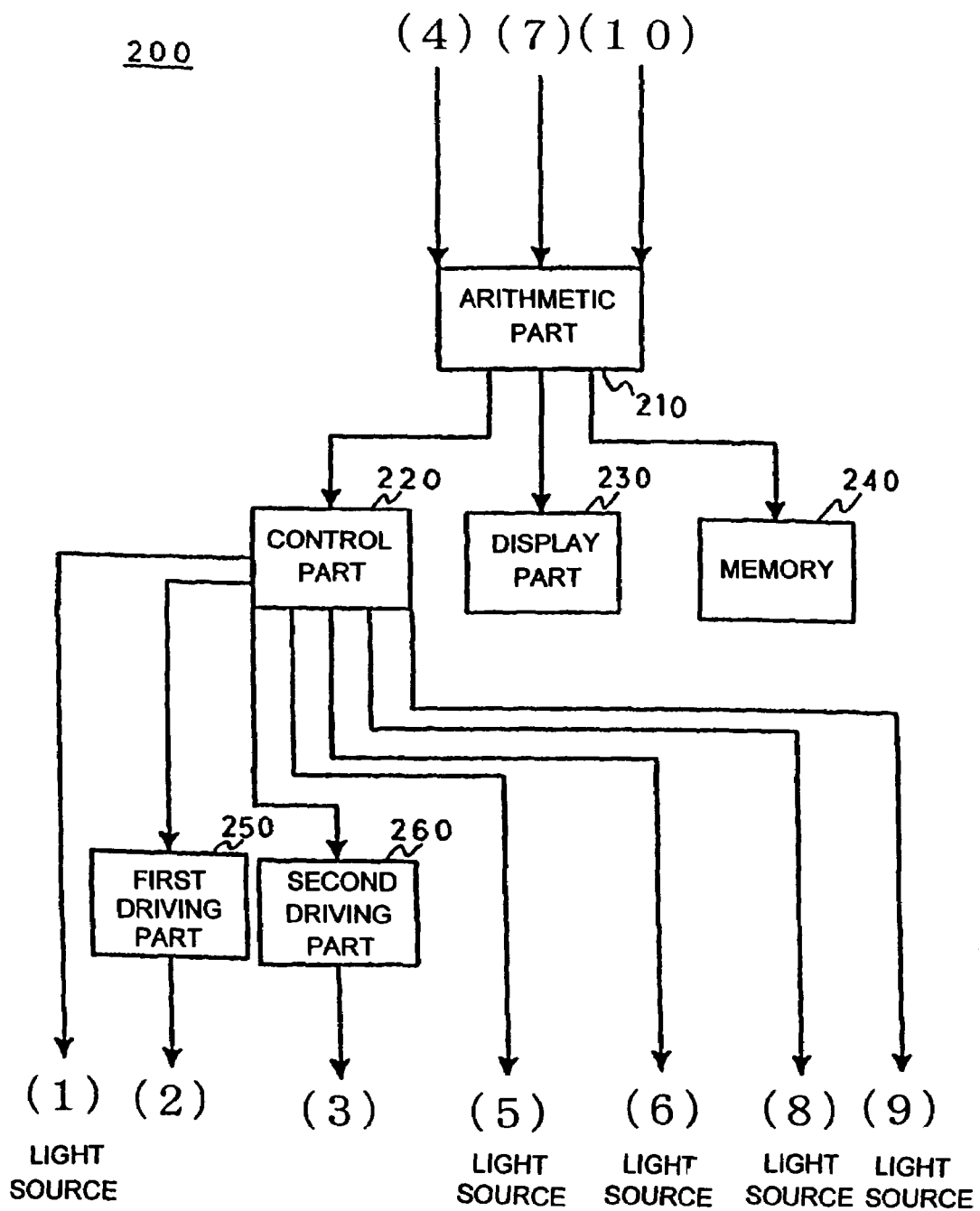
FIG. 3 is a block diagram showing a schematic electrical system 200 of the eye optical characteristic measuring apparatus of the invention.

FIG. 3 is a block diagram roughly showing an electrical system 200 of the eye optical characteristic measuring apparatus of the invention. The electrical system 200 of the eye optical characteristic measuring apparatus includes, for example, an arithmetic part 210, a control part 220, a display part 230, a memory, 240, a first driving part 250, and a second driving part 260.

The arithmetic part 210 receives a received light signal (first) (4) obtained from the first light receiving part 23, a received light signal (second signal) (7) obtained from the second light receiving part 35, and a received light signal (10) obtained from the third light receiving part 54, and performs an arithmetical operation on the origin of coordinates, a coordinate axis, movement of coordinates, rotation, ocular aberrations, corneal higher order aberrations, Zernike coefficients, aberration coefficients, a Strehl ratio, a white light MTF, a Landolt's ring pattern and the like. Besides, signals corresponding to such calculation results are outputted to the control part 220 for performing the whole control of an electric driving system, the display part 230, and the memory 240, respectively. Incidentally, the details of the arithmetic part 210 will be described later.

The control part 220 controls lighting and lights-out of the first light source part 11 on the basis of the control signal from the arithmetic part 210, or controls the first driving part 250 and the second driving part 260. For example, on the basis of the signals corresponding to the operation results in the arithmetic part 210, the control part outputs a signal (1) to the first light source part 11, outputs a signal (5) to the Placido's disk 71, outputs a signal (6) to the second light source part 31, outputs a signal (8) to the third light source part 51, outputs a signal (9) to the fourth light source part 55, and outputs signals to the first driving part 250 and the second driving part 260.

The first driving part 250 is for moving the whole first illuminating optical system 10 in the optical axis direction on the basis of, for example, the received light signal (4) inputted to the arithmetic part 210 from the first light receiving part 23, and outputs a signal (2) to a not-shown suitable lens movement means and drives the lens movement means. By this, the first driving part 250 can perform the movement and adjustment of the first illuminating optical system 10.

The second driving part 260 is for moving the whole first light receiving optical system 20 in the optical axis direction on the basis of, for example, the received light signal (4) inputted to the arithmetic part 210 from the first light receiving part 23, and outputs a signal (3) to a not-shown suitable lens movement means, and drives the lens movement means. By this, the second driving part 260 can perform the movement and adjustment of the first light receiving optical system 20.

Figure 4:
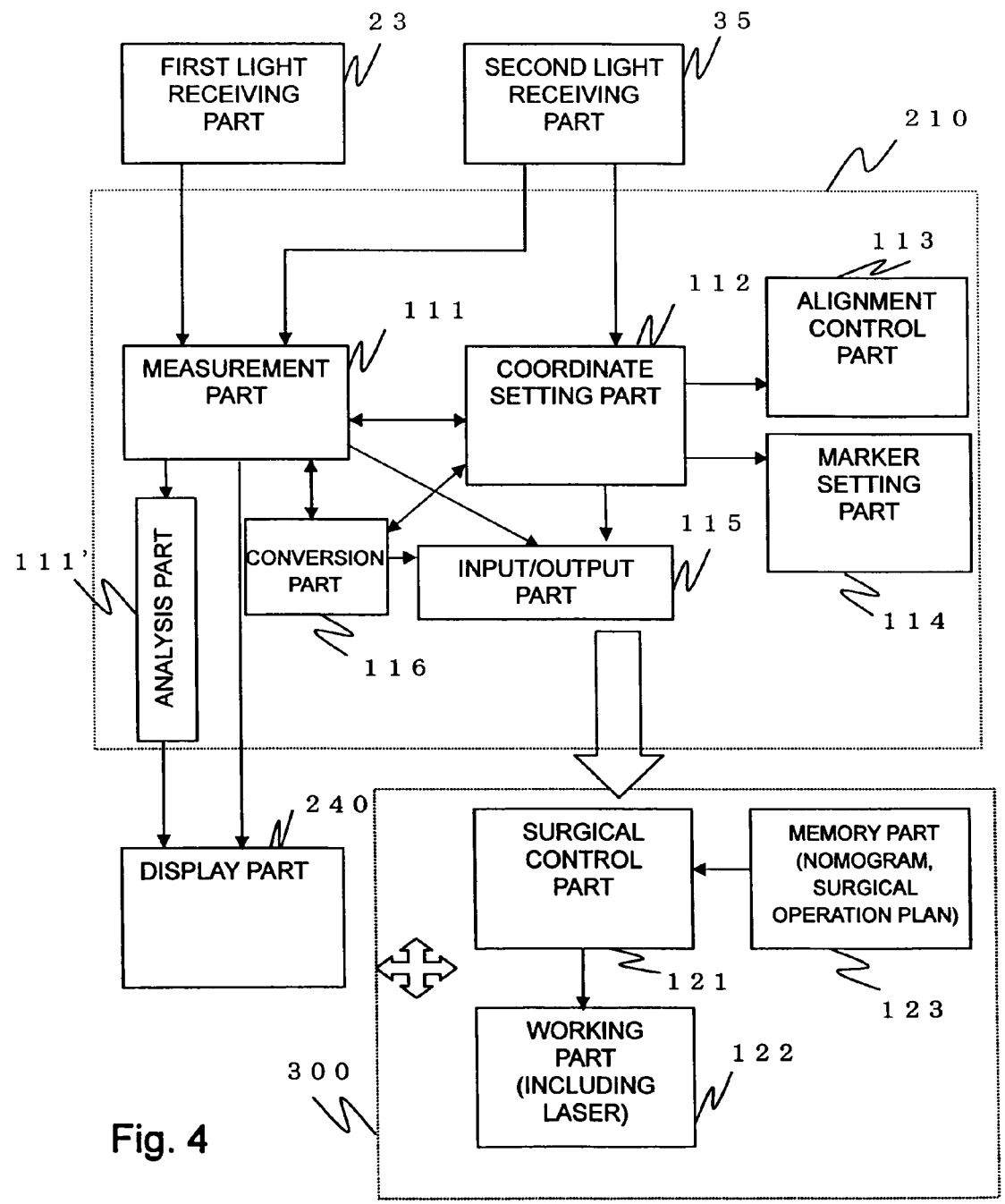
FIG. 4 is a detailed structural view relating to an arithmetic part of the eye optical characteristic measuring apparatus of the invention.

FIG. 4 is a detailed structural view concerning the arithmetic part of the eye optical characteristic measuring apparatus of the invention. The arithmetic part 210 includes a measurement part 111, an analysis part 111', a coordinate setting part 112, an alignment control part 113, a marker setting part 114, an input/output part 115, and a conversion part 116.

The first light receiving part 23 forms a first received light signal from a received light flux reflected and returned from the retina of the subject eye and guides it to the measurement part 111. The second light receiving part 35 forms a second received light signal including information of the anterior eye part from the received light flux including information relating to the feature portion of the anterior eye part of the subject eye and/or a marker formed at the anterior eye part of the subject eye, and guides it to the measurement part 111 and the coordinate setting part 112.

The measurement part 111 obtains the optical characteristics including the refractive power of the subject eye or the corneal formation on the basis of the first received light signal from the first light receiving part. Besides, the measurement part 111 sends the first received light signal to the analysis part 111' for obtaining the spot diameter of the received light flux and the scattering degree of the received light flux. Incidentally, the analysis part 111' may be constructed so as to directly receive the first received light signal from the first light receiving part 23. The details of the analysis part 111' will be described later. The measurement part 111 performs the eye optical characteristic measurement especially on the basis of the first received light signal from the first light receiving part 23. Besides, the measurement part 111 performs the cornea topography measurement especially on the basis of the second received light signal from the second light receiving part 35. Besides, the measurement part 111 performs calculation of aberrations results, and calculation of an aberration amount as the need arises, and outputs the calculation results to a surgical apparatus through the output part 115.

Figure 5:
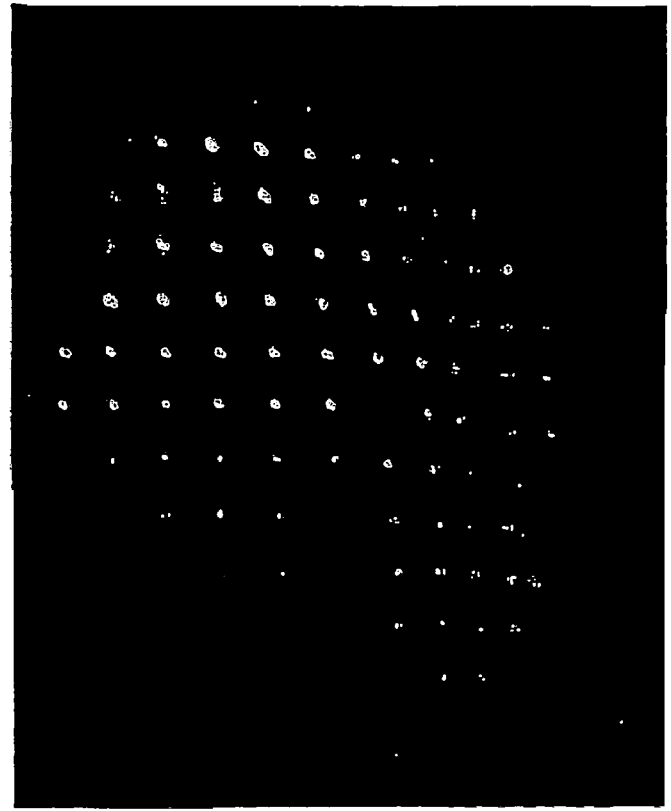
FIG. 5 is a view in which a part of an image received by a first light receiving part 23 is enlarged.
Figure 5:
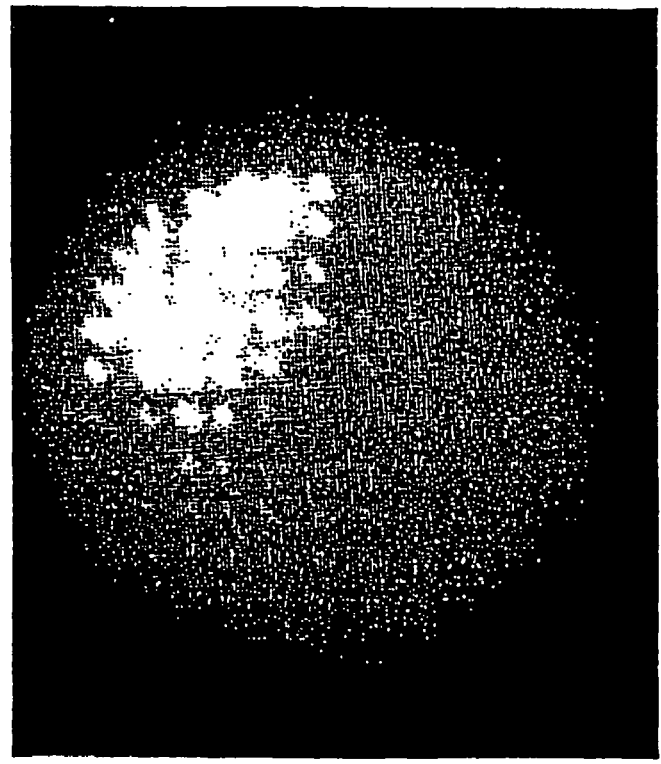

FIG. 5 is a view in which a part of an image received by the first light receiving part 23 is enlarged. The drawing (A) shows a keratoconic eye, and the drawing (B) shows an example of a Hartman image in the case of a cataractous eye. The Hartman image received by the first light receiving part 23 is, for example, the image on the basis of the reflected light from the subject eye, and includes plural area points (circles, ellipses, etc. in the drawing) in the case where the reflected light is received onto the first light receiving part 23 as light fluxes diffused generally outward through the Hartman plate 22. An optical signal of the Hartman image in this example is converted into an electrical signal, and is inputted (or captured) as the first signal to the analysis part 111'.

As stated above, the information from the Hartman-Shack wavefront sensor includes the following.

Wavefront from the barycenter of the point image (classical aberration measurement).

Local information from the blur degree of the point image (local scattering measurement).

Besides, with respect to the eye with much scattering, the blur of an image which can not be explained from only the wavefront aberrations are observed in the Hartman image. Besides, it is conceivable that the scattering amount is estimated by comparing the Hartman image obtained by the measurement with the Hartman image restored from the wavefront aberrations.

The analysis part 111' regards the plural area points as one of the received light fluxes, and obtains the spot diameter of the received light flux and the ratio of the maximum value of the light amount of the received light flux to the minimum value, that is, the scattering degree of the received light flux. The analysis part 111' obtains the distribution indicating the relation between the wavefront aberrations of the light flux incident on the light receiving optical system and the scattering degree of the received light flux. Besides, it obtains the distribution indicating the relation between the wavefront aberrations of the light flux incident on the light receiving optical system and the spot diameter of the received light flux. Incidentally, since the analysis part 111' obtains the distribution concerning the correlation among the wavefront aberrations of the light flux incident on the light receiving optical system, the catering degree of The received light flux, and the spot diameter of the received light flux, a limitation is not made to the foregoing distribution.

The analysis part 111' obtains the point spread function (PSF) by wave optical calculation from the wavefront aberrations of the light flux incident on the light receiving system, and has a calculation function to compare this with the diameter of the received light flux, that is, the point spread function (PSF) obtained by actually measuring the intensity from the image. For example, there is also a case where a comparison can be made concerning an area at an intermediate value between a maximum value and a minimum value in a square area (length of its side is almost equal to the interval of point images and one point image is generally contained in this area) including the point image, a width or the like.

Incidentally, the foregoing analysis of the analysis part 111' may correspond to plural specified point images of the Hartman image, and in this condition, as the result of one measurement, the respective point images may be analyzed in the calculation, or an average value of actually measured values may be used.

The analysis part 111' judges that as the obtained scattering degree of the received light flux of the light flux incident on the light receiving optical system as the first light receiving part becomes high, the influence of the cataract or the like becomes large, and can output that to the display part 240. Besides, the analysis part 111' judges that as the obtained spot diameter of the received light flux in the light receiving optical system as the first light receiving part becomes large, the influence of the cataract or the like becomes large, and can output that to the display part 240.

Incidentally, the judgment result, analysis result and the like by the analysis part 111' may be displayed in various forms, such as data, table, graph, three-dimensional display and graphic, on the display part 240, or may be outputted to a recording medium, such as a CD-ROM, a FD or an MO, or another apparatus by the output part.

Figure 6:
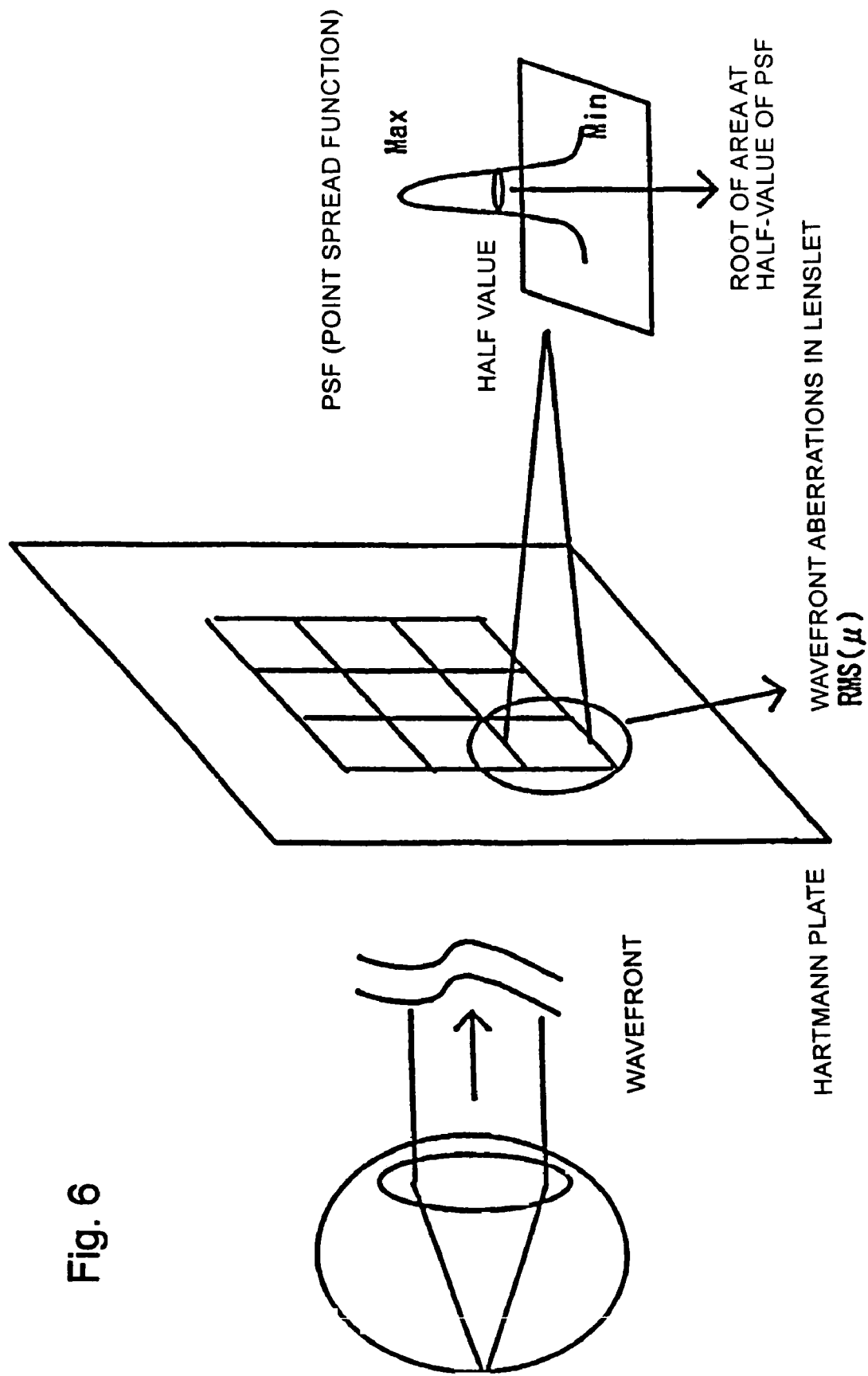
FIG. 6 is an explanatory view for obtaining a point spread function from a wavefront.

FIG. 6 is an explanatory view for obtaining the point spread function from the wavefront.

The wavefront of the light flux reflected from the retina of the subject eye passes through the Hartman plate, and the wavefront aberrations RMS in a lenslet are obtained from the inclination of the light flux at that time, and a factor such as an area of a half-value portion of the point spread function PSF is obtained.

Incidentally, the analysis part 111' can obtain a scattering coefficient in a manner as indicated by a following expression.

$$\text{Index} = \sqrt{A} - (a \cdot RMS_{SL} - c) \quad (1)$$

Index: scattering prediction coefficient (also called scattering prediction index)
A: area (average) of the half-value portion of the PSF
$RMS_{SL}$: wavefront aberrations (average) in the lenslet portion
a: constant obtained by non-cataractous eye measurement
c: scattering correction constant of measuring apparatus.

Figure 7:
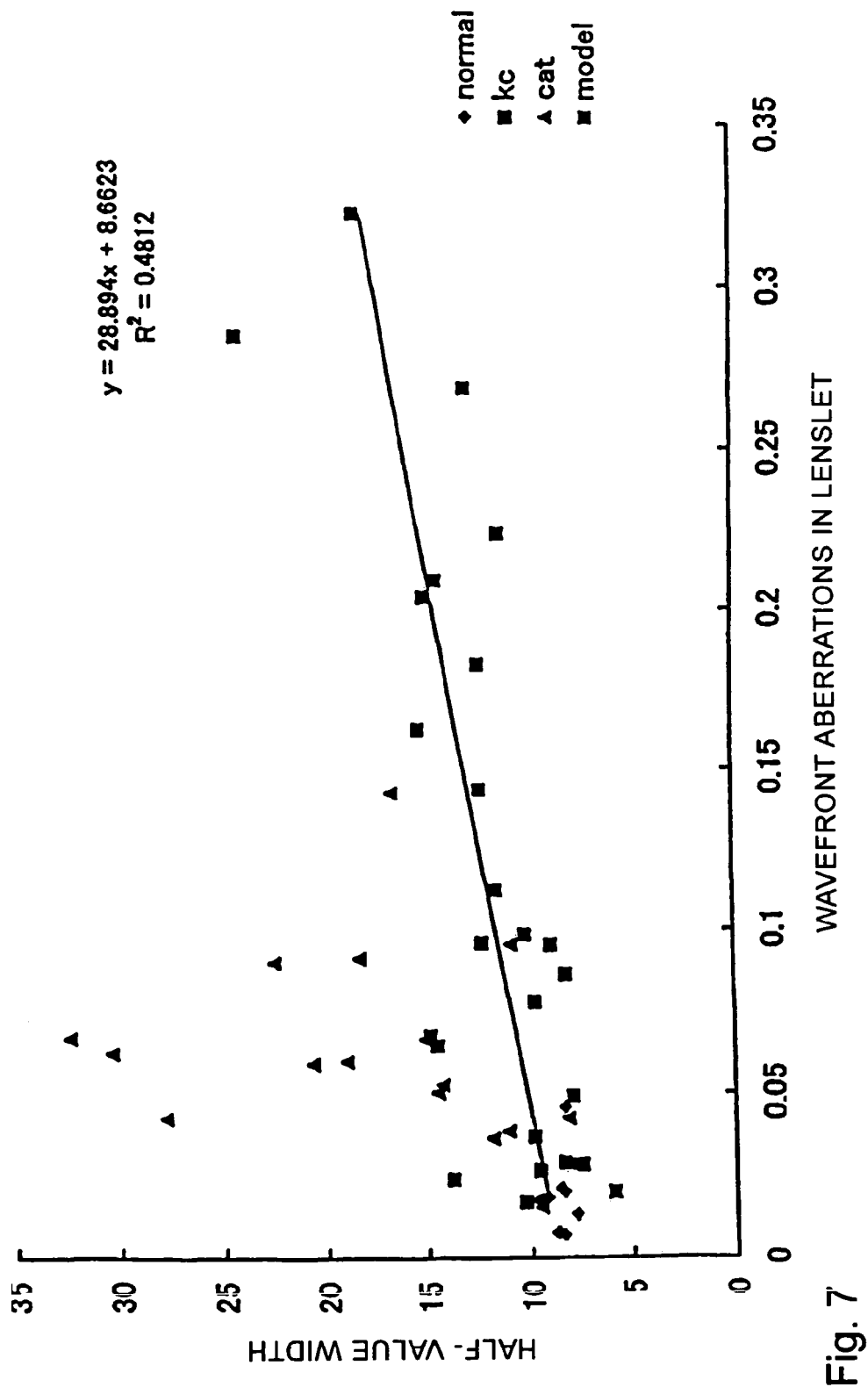
FIG. 7 is a view (1) of experimental results according to an eye optical characteristic measuring apparatus of an embodiment.

Incidentally, a and c are coefficients of a regression line obtained in FIG. 7 by using a keratoconic eye and a normal eye. In this case, a: first-order coefficient of 28.894, and c: constant term of 8.6623.

In the actual analysis, there is also a case where the area A is obtained for the plural point images of the Hartman image, this is subjected to the processing of the above expression and is averaged to obtain the result of one measurement.

This scattering coefficient is obtained for the respective lenslets by using various factors of the respective lenslets.

Figure 9:
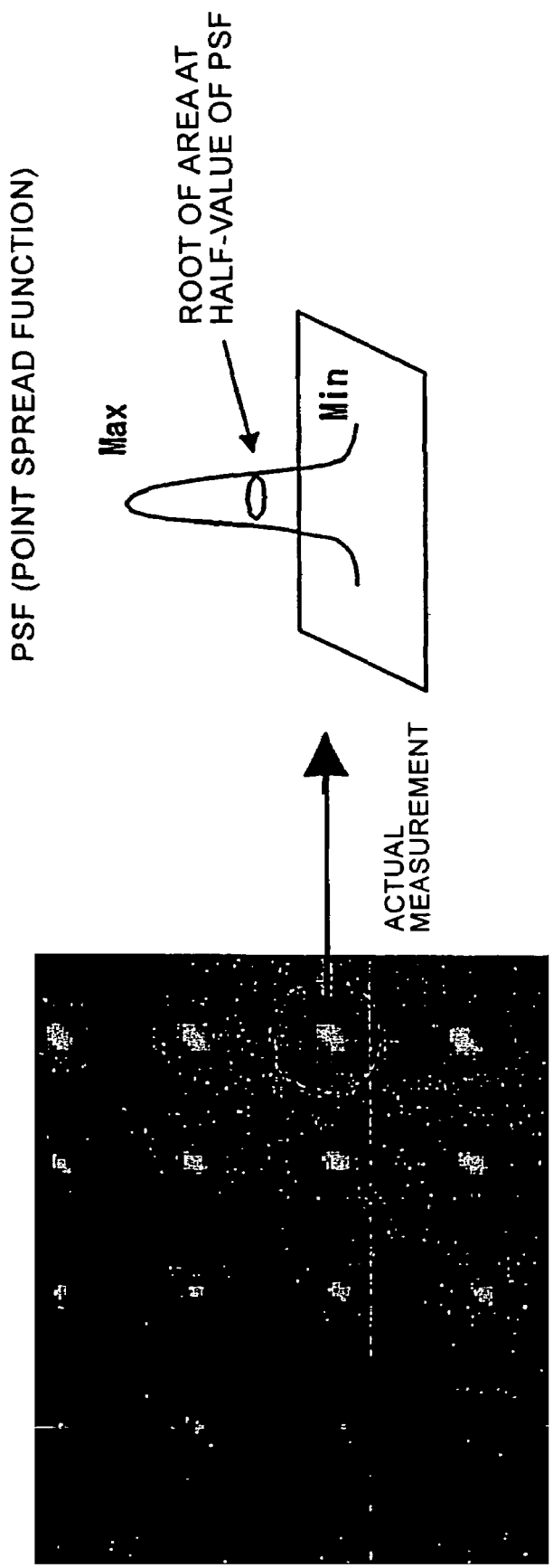
FIG. 9 is an explanatory view showing a picture of point images and point image intensity.

The relation between the picture of the point image and the point image intensity is as shown in FIG. 9. At this time, when such a CCD that a gamma value indicating a relation between a light amount and an output becomes 1 is adopted, since the intensity distribution of the PSF is proportional to the digital count (computer count) of the CCD, the measurement is easy. Here, the minimum intensity and the maximum intensity are obtained in a quadrangle 0.6 mm square with the point image as the center, and a Michelson contrast ratio can also be obtained from this, and an area at an intermediate point between the minimum intensity and the maximum intensity can also be obtained.

Besides, a method is also conceivable in which instead of the wavefront aberrations $RMS_{SL}$, the point spread function (PSF) of FIG. 6 is obtained from the wavefront aberrations by calculation, and this is compared with the actually measured PSF.

In the case where this method is used, it becomes unnecessary to make the correction using the eye with little scattering, such as the normal eye or the keratoconus, and the reliability of the result is increased. On the other hand, in the former method in which the wavefront aberrations and the PSF are compared with each other, since there is no trouble to calculate the PSF by calculation, the total processing time can be made considerably short.

The coordinate setting part 112 converts signals of a first and a second coordinate systems corresponding to the pupil of the subject eye included in the first and the second received light signals into signals of reference coordinate systems, respectively. The coordinate setting part 112 obtains a pupil edge and a pupil center on the basis of the respective signals of the first and the second coordinate systems.

Besides, the coordinate setting part 112 decides the origin of coordinates and the direction of a coordinate axis on the basis of the second received light signal including feature signals of the anterior eye part of the subject eye. Besides, the coordinate setting part 112 obtains the origin of the coordinates, and the rotation and movement of the coordinate axis on the basis of at least one of the feature signals of the anterior eye part of the subject eye of the second received light signal, and correlates the measurement data with the coordinate axis. Incidentally, the feature portion includes at least one of a pupil position, a pupil center, a corneal center, an iris position, an iris pattern, a pupil shape, and a limbus shape. For example, the coordinate setting part 112 sets the origin of the coordinates, such as the pupil center or the corneal center. The coordinate setting part 112 forms the coordinate system on the basis of the feature signal corresponding to the image of the feature portion of the anterior eye part of the subject eye included in the second received light signal. Besides, the coordinate setting part 112 forms the coordinate system on the basis of a marker signal included in the second received light signal and concerning a marker provided on the subject eye, and a signal concerning the anterior eye part of the subject eye. The coordinate setting part 112 can decide the origin of the coordinates and the direction of the coordinate axis on the basis of the second received light signal including the marker signal. The coordinate setting part 112 obtains the origin of the coordinates on the basis of the marker signal in the second received light signal, obtains the rotation and movement of the coordinate axis on the basis of any one of the feature signals of the anterior eye part of the subject eye in the second received light signal, and can correlate the measurement data with the coordinate axis. Alternatively, the coordinate setting part 112 obtains the origin of the coordinates on the basis of at least one of the feature signals concerning the anterior eye part in the second received light signal, obtains the rotation and movement of the coordinate axis on the basis of the marker signal in the second received light signal, and may correlate the measurement data with the coordinate axis. Alternatively, the coordinate setting part 112 obtains the origin of the coordinates and the rotation and movement of the coordinate axis on the basis of at least one of the feature signals of the anterior eye part of the subject eye in the second received light signal, and may correlate the measurement data with the coordinate axis.

The conversion part 116 correlates the first and the second optical characteristics of the subject eye obtained by the measurement part 111 through the respective reference coordinate systems formed by the coordinate setting part and combines them. Besides, the conversion part 116 performs conversion to the reference coordinate system by making the pupil center obtained by the coordinate setting part 112 the origin.

One of, two or more of, or all of the first illuminating optical system 10, the first light receiving optical system 20, the second light receiving optical system 30, the common optical system 40, the adjusting optical system 50, the second illuminating optical system 70, and the second light sending optical system 80 are suitably provided in an alignment part of the optical system 100. The alignment control part 113 can move this alignment part according to the movement of the subject eye and in accordance with the operation result of the coordinate setting part 112 on the basis of the second received light signal obtained by the second light receiving part. On the basis of the coordinate system set by the coordinate setting part 112, the marker setting part 114 forms a marker correlated with the coordinate system on the anterior eye part of the subject eye. The input/output part 115 is an interface for outputting data and operation results of the aberration amount, the origin of coordinates, the coordinate axis, the rotation and movement of the coordinate axis, and the ablation amount to the surgical apparatus. A display part 240 displays the optical characteristic of the subject eye obtained by the measurement part 111 in relation to the coordinate system formed by the coordinate setting part.

A surgical apparatus 300 includes a surgical control part 121, a working part 122, and a memory part 123. The surgical control part 121 controls the working part 122, and controls a surgical operation such as corneal refractive surgery. The working part 122 includes a laser for the surgical operation such as corneal refractive surgery. The surgical memory part 123 stores data for the surgical operation, such as data concerning cutting, a nomogram, a surgical schedule and the like.

Next, FIG. 7 shows a view (1) of experimental results by the eye optical characteristic measuring apparatus of this embodiment. In this embodiment, for the confirmation of measurement of eye optical characteristics, 9 normal eyes, 24 keratoconic eyes, and 17 cataractous eyes were measured, and the half-value widths were obtained. Incidentally, in the drawing, the normal eye (normal) is indicated by rhombus (♦), the keratoconic eye (keratoconus) is indicated by square (■), and the cataractous eye (cataract) is indicated by triangle (▲).

The measurement part 111 or the analysis part 111' analyses the output result from the first received light signal (4) by a specified analytic method. That is, the blur of the received laser light is considered to be the scattered light, and there is obtained the half-value width (square root of area for apots) on the basis of the size of the spot diameter of the received light flux or the ratio of the maximum received light amount of the received light flux to the minimum received light amount, that is, the scatter intensity ratio (minimum intensity/maximum intensity, scattering coefficient) is obtained. Besides, the measurement part 111 or the analysis part 111' prepares the distribution (FIG. 6) of the spot diameter of the received light flux or the distribution of the scatter intensity ratio of the received light flux with respect to the phase (standard deviation) of the wavefront aberrations incident on the first light receiving part 23, which are obtained by the light receiving optical system.

Incidentally, with respect to the cataractous eye, since it deviates from the approximated straight line, it can be differentiated from the keratoconic eye. That is, on the basis of the obtained straight line approximation, a test subject who is suspected of having the cataractous eye is discriminated, and this can be used as information for making a decision about the surgery and remedy.

Figure 8:
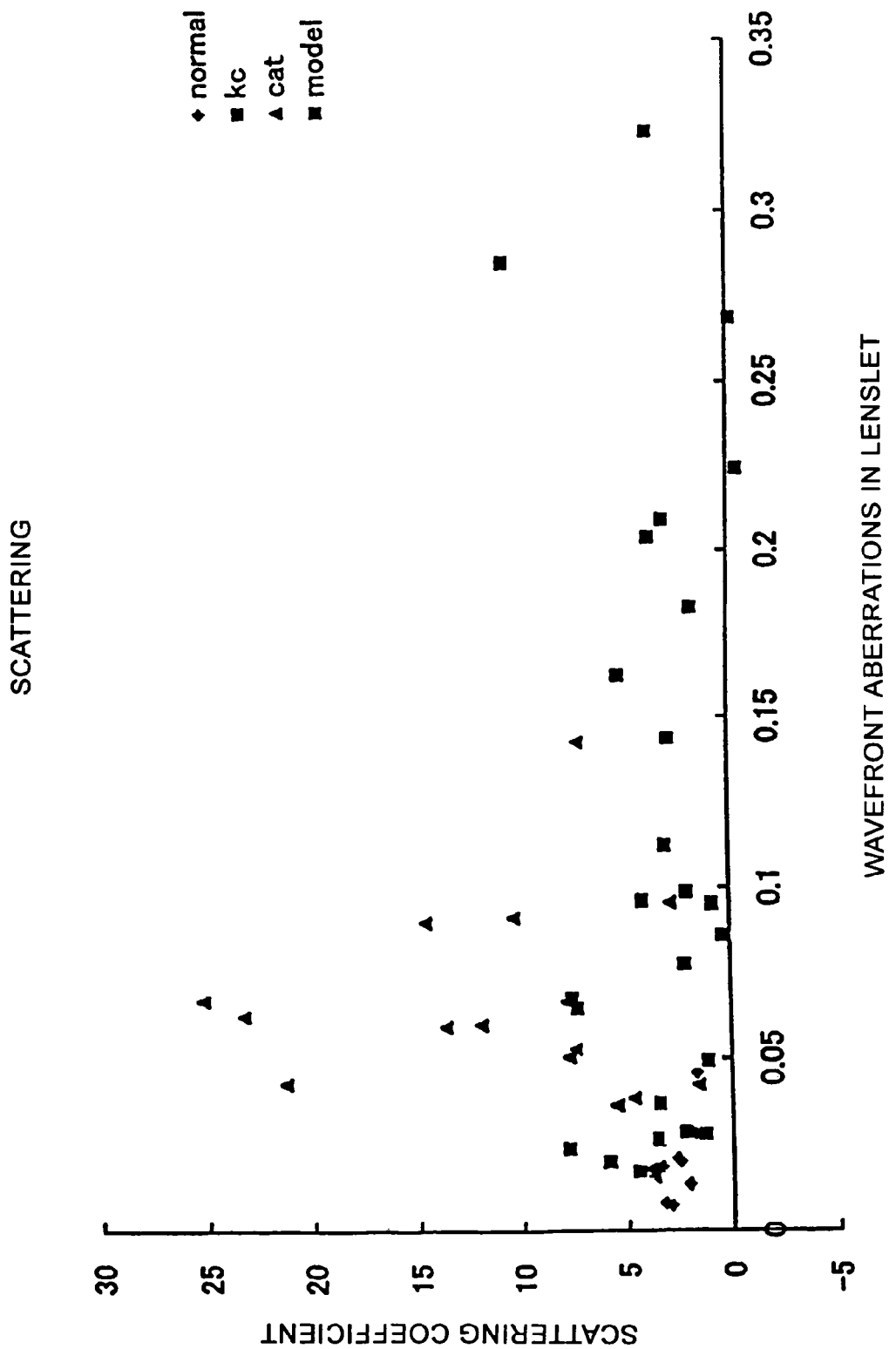
FIG. 8 is a view (2) of experimental results according to the eye optical characteristic measuring apparatus of the embodiment.

FIG. 8 shows a view (2) of experimental results by the eye optical characteristic measuring apparatus of this embodiment.

In this drawing, the correction by eq. (1) is added to the half-value width of FIG. 7. The vertical axis indicates an amount obtained by subtracting a value obtained by substituting the wavefront aberrations of the lenslet into eq. (1) from the half-value width. In non-cataractous eyes, obtained values are arranged substantially horizontally. In the cataractous eye or an eye with large scattering, this value becomes large. Besides, a model eye whose scattering can be neglected is measured, and it is also conceivable that a correction is further performed by this measurement value to make the estimate of the scattering amount more accurate. Although the method used here is suitable for the measurement of the crystalline lens scattering, it is also conceivable to apply this to measurement of retina scattering or the like.

As the result of the analysis, as an example, there were obtained SIR (scatter intensity ratio)=0.460±0.067 for the normal eye, SIR=0.495±0.098 for the keratoconic eye, and SIR=0.667±0.148 for the cataractous eye (ANOVA (dispersion analysis), P<0.01). Besides, the scattering coefficient was 2.61±0.70 for the normal eye, 3.38±2.73 for the keratoconic eye, and 10.13±7.25 for the cataractous eye. Besides, although there was no significant difference between the normal eye and the keratoconic eye (P<0.122), there was significant difference between the normal eye and the cataractous eye, and between the keratoconic eye and the cataractous eye (P<0.01). Incidentally, 9 normal eyes with little scattering, 24 keratoconic eyes, and 17 cataractous eyes with large scattering were measured.

By this, possibility of measurement of the scattering amount by the Hartman-Shack wavefront sensor is suggested. After this, evaluation standards comparable to visual functions are examined, and clinical effectiveness is confirmed.

INDUSTRIAL APPLICABILITY

According to the present invention, it is possible to provide the eye optical characteristic measuring apparatus which enables the scattering measurement by the Hartman-Shack wavefront sensor whose main object is wavefront aberration measurement, and can accurately estimate the visual functions by performing the scattering measurement.

Besides, according to the invention, as the scattering measurement method by the Hartman-Shack wavefront sensor, the scattering analytic method is developed in which the scattering amount is estimated from the scatter intensity ratio (SIR) of background light of the Hartman image, and the eye optical characteristic measuring apparatus which can enable simultaneous measurement of scattering by the optical system of the Hartman-Shack wavefront sensor can be provided.

Besides, according to the invention, the eye optical characteristic measuring apparatus can be provided which can make the judgment that from the distribution of relations between the wavefront aberrations of the light flux incident on the light receiving optical system and the scattering degree of the received light flux, as the wavefront aberrations of the light flux incident on the light receiving optical system and the scattering degree of the received light flux become nigh, the influence of the cataract becomes large.

Besides, according to the invention, the eye optical characteristic measuring apparatus can be provided which can make the judgment that from the distribution of relations among the wavefront aberrations of the light flux incident on the light receiving optical system, the scattering degree of the received light flux, and the spot diameter of the received light flux, as the wavefront aberrations of the light flux incident on the light receiving optical system and the scattering degree of the received light flux become high, or as the spot diameter of the received light flux becomes large, the influence of the cataract becomes large.

The invention claimed is:

1. An eye optical characteristic measuring apparatus, comprising:
    a light source part for emitting a light flux of a specified wavelength;
    an illumination optical system for illuminating a minute area on a retina of a subject eye with the light flux from the light source part;
    a light receiving optical system for receiving a part of a reflected light flux which is the light flux emitted from the light source part and reflected by the retina of the subject eye, through a conversion member for converting it into at least substantially 17 beams;
    a light receiving part for receiving a received light flux guided by the light receiving optical system to form signals; and
    an arithmetic part for obtaining wavefront aberrations of the light flux incident on the light receiving optical system and a spot diameter of the received light flux on the basis of the signals from the light receiving part,
    wherein the arithmetic part obtains a point spread function based on a signal from the light receiving part, and estimates crystalline lens scattering and retina scattering by comparing the obtained point spread function with a point spread function obtained from the wavefront aberrations of the subject eye which are obtained on the basis of the signals from the light receiving part.

2. An eye optical characteristic measuring apparatus according to claim 1,
wherein the arithmetic part obtains a scattering degree of the received light flux on the basis of the signals from the light receiving part and, obtains a distribution of relations between the wavefront aberrations of the light flux incident on the light receiving optical system and the scattering degree of the received light flux.

3. An eye optical characteristic measuring apparatus according to claim 2,
wherein the arithmetic part is constructed to judge that, as the scattering degree of the received light flux becomes high, an influence of a cataract becomes large.

4. An eye optical characteristic measuring apparatus according to claim 3,
further comprising a display part or an output part for displaying or outputting a judgment result by the arithmetic part.

5. An eye optical characteristic measuring apparatus according to claim 2,
further comprising a display part for displaying the distribution obtained by the arithmetic part.

6. An eye optical characteristic measuring apparatus according to claim 1,
wherein the arithmetic part obtains a distribution of relations between the wavefront aberrations of the light flux incident on the light receiving optical system and the spot diameter of the received light flux.

7. An eye optical characteristic measuring apparatus according to claim 6,
wherein the arithmetic part is constructed to judge that as the spot diameter of the received light flux becomes large, an influence of cataract or the like becomes large.

8. An eye optical characteristic measuring apparatus according to claim 1,
wherein the arithmetic part obtains a scattering degree of the received light flux on the basis of the signals from the light receiving part and, obtains a distribution of relations among the wavefront aberrations of the light flux incident on the light receiving optical system, the scattering degree of the received light flux, and a spot diameter of the received light flux.

9. An eye optical characteristic measuring apparatus according to claim 8,
wherein the arithmetic part is constructed to judge that, as the obtained wavefront aberrations of the light flux incident on the light receiving optical system and the scattering degree of the received light flux become high, or as the spot diameter of the received light flux becomes large, an influence of a cataract large.

10. An eye optical characteristic measuring apparatus, comprising:
a light source part for emitting a light flux of a specified wavelength;
an illumination optical system for illuminating a minute area on a retina of a subject eye with the light flux from the light source part;
a light receiving optical system for receiving a part of a reflected light flux which is the light flux emitted from the light source part and reflected by the retina of the subject eye, through a conversion member for converting it into at least substantially 17 beams;
a light receiving part for receiving a received light flux guided by the light receiving optical system to form signals; and
an arithmetic part for obtaining a point spread function obtained from wavefront aberrations of the light flux incident on the light receiving optical system and an actually measured spot diameter of the received light flux on the basis of the signals from the light receiving parts,
wherein crystalline lens scattering and retina scattering are estimated by subtracting a diameter of the point spread function from the obtained spot diameter of the received light flux.

11. An eye optical characteristic measuring apparatus according to claim 10,
wherein the arithmetic part obtains a distribution of relations between the point spread function obtained from the wavefront aberrations of the light flux incident on the light receiving optical system and a scattering degree of the received light flux.

12. An eye optical characteristic measuring apparatus according to claim 10,
wherein the arithmetic part is constructed to judge that, as a diameter of the obtained point spread function and/or the spot diameter of the received light flux becomes high, an influence of cataract or the like becomes large.

13. An eye optical characteristic measuring apparatus according to claim 10,
wherein the arithmetic part obtains a distribution of relations between a diameter of the point spread function obtained from the wavefront aberrations of the light flux incident on the light receiving optical system and the spot diameter of the received light flux.

14. An eye optical characteristic measuring apparatus comprising:
a light source part for emitting a light flux of a specified wavelength;
an illumination optical system for illuminating a minute area on a retina of a subject eye with the light flux from the light source part;
a light receiving optical system for receiving a part of a reflected light flux which is the light flux emitted from the light source part and reflected by the retina of the subject eye, through a conversion member for converting it into at least 17 beams;
a light receiving part for receiving a received light flux guided by the light receiving optical system to form signals; and
an arithmetic part for obtaining wavefront aberrations of the light flux incident on the light receiving optical system and a spot diameter of the received light flux on the basis of the signals from the light receiving part,
wherein the arithmetic part obtains a minimum intensity and a maximum intensity in predetermined range with a point image as the center, and obtains a Michelson contrast ratio or an area at an intermediate point between the minimum intensity and the maximum intensity on the basis of this, and estimates crystalline lens scattering and retina scattering.

* * * * *